United States Patent [19]
Dann

[11] Patent Number: 6,148,236
[45] Date of Patent: Nov. 14, 2000

[54] CANCER TREATMENT SYSTEM EMPLOYING SUPPLEMENTED THERMAL THERAPY

[75] Inventor: Mitchell Dann, Jackson, Wyo.

[73] Assignee: Urologix, Inc., Minneapolis, Minn.

[21] Appl. No.: 09/185,922

[22] Filed: Nov. 4, 1998

[51] Int. Cl.[7] .............................. A61N 5/00; A61N 5/02
[52] U.S. Cl. ................... 607/101; 600/2; 600/8; 600/12; 606/33; 607/102; 607/156
[58] Field of Search .............................. 607/99–102, 105, 607/113, 156; 600/8, 12, 2; 606/33

[56] References Cited

U.S. PATENT DOCUMENTS 4,702,228   10/1987   Russel, Jr. et al. ...................... 128/1.2

(List continued on next page.)

OTHER PUBLICATIONS

Thermoregulation in the canine prostate during transurethral microwave hyperthermia, part I: temperature response by Xu et al., *International Journal of Hyperthermia*, vol. 14, No. 1, Jan.–Feb. 1998.

"Hyperthermia may decrease the development of telangiectasia after radiotherapy" by Van Der Zee et al., *International Journal of Hyperthermia*, vol. 14, No. 1, Jan.–Feb. 1998.

"Comparison of Radical Prostactetomy and Iodine 125 Interstitial Radiotherapy for the Treatment of Clinically Localized Prostate Cancer: a 7–Year Biochemical (PSA) Progression Analysis", by Polascik et al., *Urology*, vol. 51, No. 6, Jun. 1998.

"Can mild hyperthermia improve tumour oxygenation?", by Horsman et al., *International Journal of Hyperthermia*, vol. 13, No. 2, Mar.–Apr. 1997.

"Hyperthermia as an adjuvant to radiation therapy of recurrent or metastatic malignant melanoma. A multicentre randomized trial by the European Society for Hyperthermic Oncology," by Overgaard et al., *International Journal of Hyperthermia*, vol. 12, No. 1, Jan.–Feb. 1996.

"Biological Rationale and Clinical Experience with Hyperthermia" by Engin, *Controlled Clinical Trials*, vol. 17, No. 4, Aug. 1996.

"Interstitial radiation and hyperthermia in the Dunning R3327 prostate tumour model: therapeutic efficacy depends on radiation dose–rate, sequence and frequency of heating" by Peschke et al., *International Journal of Radiation Biology*, vol. 70, No. 5, Nov. 1996.

"Effect of hyperthermia 42.5° C/120 min on 3H–thymidine incorporation in different tissue components of Wilms'tumors: an in vitro study" by Willnow et al., *Klinische Padiatrie*, Jul.–Aug. 1996.

"Hyperthermia Enhances the Cytotoxicity against Hypoxic Cells of RP–170, a New 2–Nitroimidazole Nucleoside Hypoxic Cell Sensitizer" by Emi et al., *International Journal of Cancer Research and Treatment, Oncology*, vol. 52, No. 1, Jan.–Feb. 1995.

"Randomised trial of hyperthermia as adjuvant to radiotherapy for recurrent or metastatic malignant melanoma" by Overgaard et al., *The Lancet*, vol. 345, No.8949, Mar. 4, 1995.

"Hyperfractionated radiation in combination with local hyperthremia in the treatment of advanced squamous cell carcinoma of the head and neck: a phase I–II study", by Amicheitt et al., *Radiotheraphy and Oncology*, vol. 45, No. 2, Nov. 1997.

*Primary Examiner*—Lee Cohen
*Attorney, Agent, or Firm*—Kinney & Lange, P.A.

[57] ABSTRACT

A system for treatment of a target volume of cancerous tissue comprises a probe carrying a microwave antenna positioned in a body cavity proximate the target volume. At least one energy-emitting element is placed in the target volume. The microwave antenna is energized so that energy emitted from the antenna and the energy-emitting element necroses cancerous tissue in the target volume.

11 Claims, 2 Drawing Sheets

U.S. PATENT DOCUMENTS

| | | | |
|---|---|---|---|
| 4,784,116 | 11/1988 | Russel, Jr. et al. | 128/1.2 |
| 5,133,710 | 7/1992 | Carter, Jr. et al. | 606/28 |
| 5,197,940 | 3/1993 | Sievert et al. | 600/9 |
| 5,405,309 | 4/1995 | Carden, Jr. | 600/3 |
| 5,429,583 | 7/1995 | Paulus et al. | 600/2 |
| 5,531,662 | 7/1996 | Carr | 600/2 |
| 5,540,679 | 7/1996 | Fram et al. | 606/27 |
| 5,620,479 | 4/1997 | Diederich | 607/97 |
| 5,964,791 | 10/1999 | Bolmsjo | 607/100 |

CANCER TREATMENT SYSTEM EMPLOYING SUPPLEMENTED THERMAL THERAPY

BACKGROUND OF THE INVENTION

The present invention relates to treatment of cancer, and more particularly to a cancer treatment system delivering thermal energy from a body cavity to a cancerous volume of tissue while supplementing the effects of the thermal therapy with a complementary treatment mechanism introduced into the cancerous volume of tissue.

Many devices have been proposed for intracavitary treatment of diseased tissue. One of the most successful devices is disclosed in U.S. Pat. No. 5,330,518 entitled METHOD FOR TREATING INTERSTITIAL TISSUE ASSOCIATED WITH MICROWAVE THERMAL THERAPY, which is hereby incorporated by reference. The disclosed device is inserted into a bodily conduit, such as a urethra, for treating a target volume of tissue, such as a prostate. The device includes a microwave antenna and a cooling system, so that the target volume can be heated to a temperature greater than about 45° C. while maintaining the bodily conduit at a safe temperature. The device may be operated to necrose the target volume of diseased tissue while preserving adjacent healthy tissue and the healthy tissue of the bodily conduit. The intracavitary nature of the device with cooling of the urethra minimizes the trauma associated with the treatment by avoiding puncturing or removing the urethra which occur with surgery and other more invasive procedures. This also minimizes the requirement for anesthesia during the procedure, the post-treatment discomfort such as dysuria and long term morbidity effects such as incontinence or impotence which are associated with more invasive procedures such as surgery and interstitial therapies.

In some situations, a cancerous volume of tissue is located a distance from the bodily conduit that makes it quite difficult to heat the diseased tissue to a sufficient temperature for a sufficient period of time to necrose the diseased tissue without harming intervening healthy tissue, particularly the wall of the bodily conduit. For example, when the prostate is afflicted with cancer, prostate tissue located near the periphery of the prostate, known as the prostatic capsule, is often among the tissue that is cancerous. The distance from the urethra to the outside of the prostatic capsule is so large as to present significant hurdles to thermally treating the cancerous tissue to cause necrosis while preserving the urethral wall and controlling the temperature at the rectum, which is susceptible to thermal damage.

Another method of treating cancerous tissue involves interstitial implantation of heat-emitting or radiation-emitting seeds. For example, a plurality of seeds may be implanted within prostate tissue through the perineum to treat prostate cancer. While this method is effective to deliver a sufficient dose of thermal energy or radiation to the target volume of diseased tissue, it is highly invasive and significant irritating symptoms and voiding dysfunction often occur following seed therapy as a result of both the multiple transperineal punctures required to insert the seeds and the effect of radiation over time. The long term effects of interstitial seed implantation are only known in patients with relatively low grade cancers, and even these results appear to be less effective than traditional surgery. A likely explanation for the lesser success of seed therapy is that it is difficult to precisely locate the position and extent of cancer in the prostate, and since the entire prostate is not removed as with surgery, there is a possibility that the radiation from the seed may leave some cancerous portions of the prostate untreated. There is even some data indicating that recurrent cancers that are not fully treated are more serious and faster growing than the original cancers. Therefore, interstitial seed therapy alone does not present an optimal treatment alternative for prostate cancer.

SUMMARY OF THE INVENTION

The present invention is a system for treating a target volume of cancerous tissue by supplemented thermal therapy. A probe carrying a microwave antenna is positioned in a body cavity proximate the target volume. A needle carrying an energy-emitting element is inserted in the target volume to implant the energy-emitting element. The microwave antenna is energized to necrose cancerous tissue in the target volume. The energy-emitting element is operable to necrose cancerous tissue in the vicinity of the energy-emitting element in the target volume. In one embodiment, the probe is adapted to be inserted into a urethra and the needle is insertable through a perineum into a prostate. The energy-emitting element may comprise a radiation-emitting seed or a seed that elevates in temperature in the presence of a magnetic field, for example.

DETAILED DESCRIPTION OF THE PREFERRED EMBODIMENTS

Throughout this detailed description, the present invention will be described as it pertains to transurethral treatment of prostate cancer. It will be understood by those skilled in the art that certain principles of the present invention may also be applied to treatment of other cancers from nearby body conduits.

Figure 1:
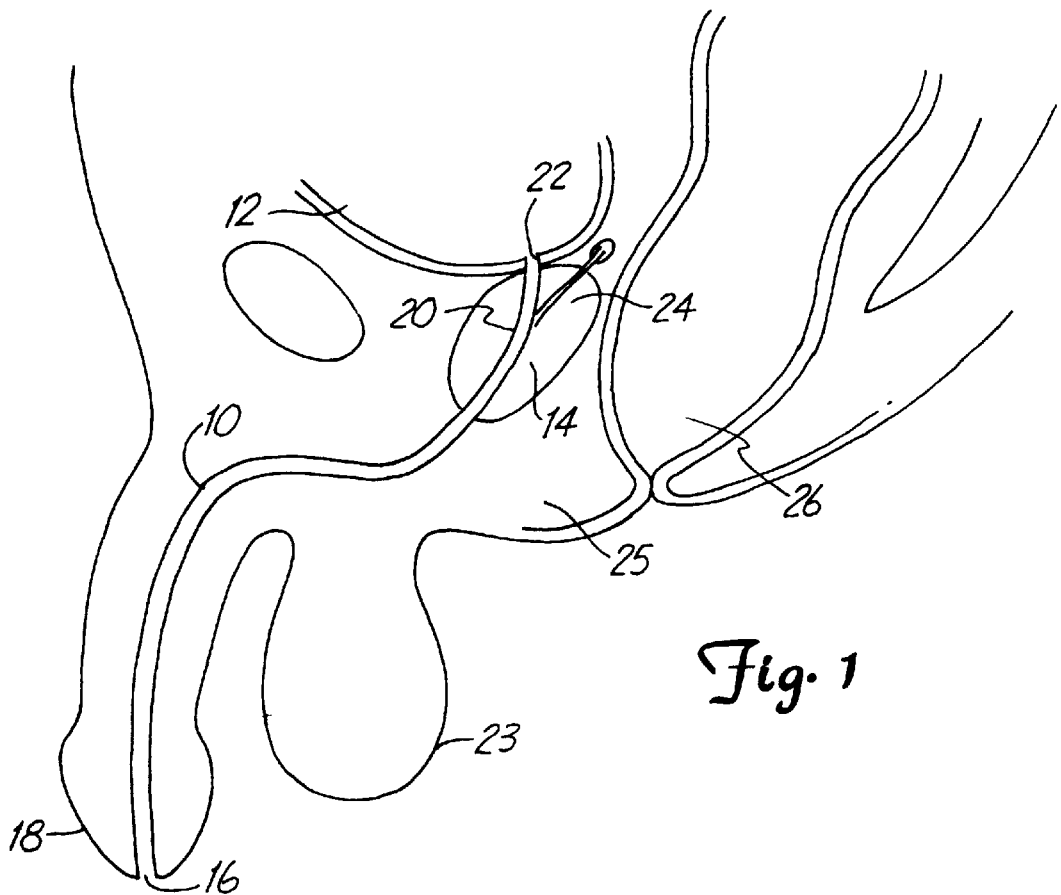
FIG. 1 is a vertical sectional view of a male pelvic region.

FIG. 1 is a vertical sectional view of a male pelvic region showing the relative position of urinary organs near the prostate 14. Urethra 10 is a duct leading from bladder 12, through prostate 14 and out orifice 16 of penis end 18. Urethra 10 includes a prostatic portion 20 passing through prostate 14. Perineum 25 is located between scrotum 23 and rectum 26. When prostate 14 is afflicted with cancer, tissue around the periphery of the prostatic capsule is typically among the tissue that is determined to contain cancer. In order to treat the cancerous tissue around the periphery of prostate 14, it is necessary to deliver energy to the cancerous tissue with sufficient intensity and for a sufficient time to destroy the cancerous tissue. It is also important to avoid intolerable damage to urethra 10 and to adjacent healthy tissues, such as intervening tissue in prostate 14, ejaculatory duct 24 and rectum 26.

Figure 2:
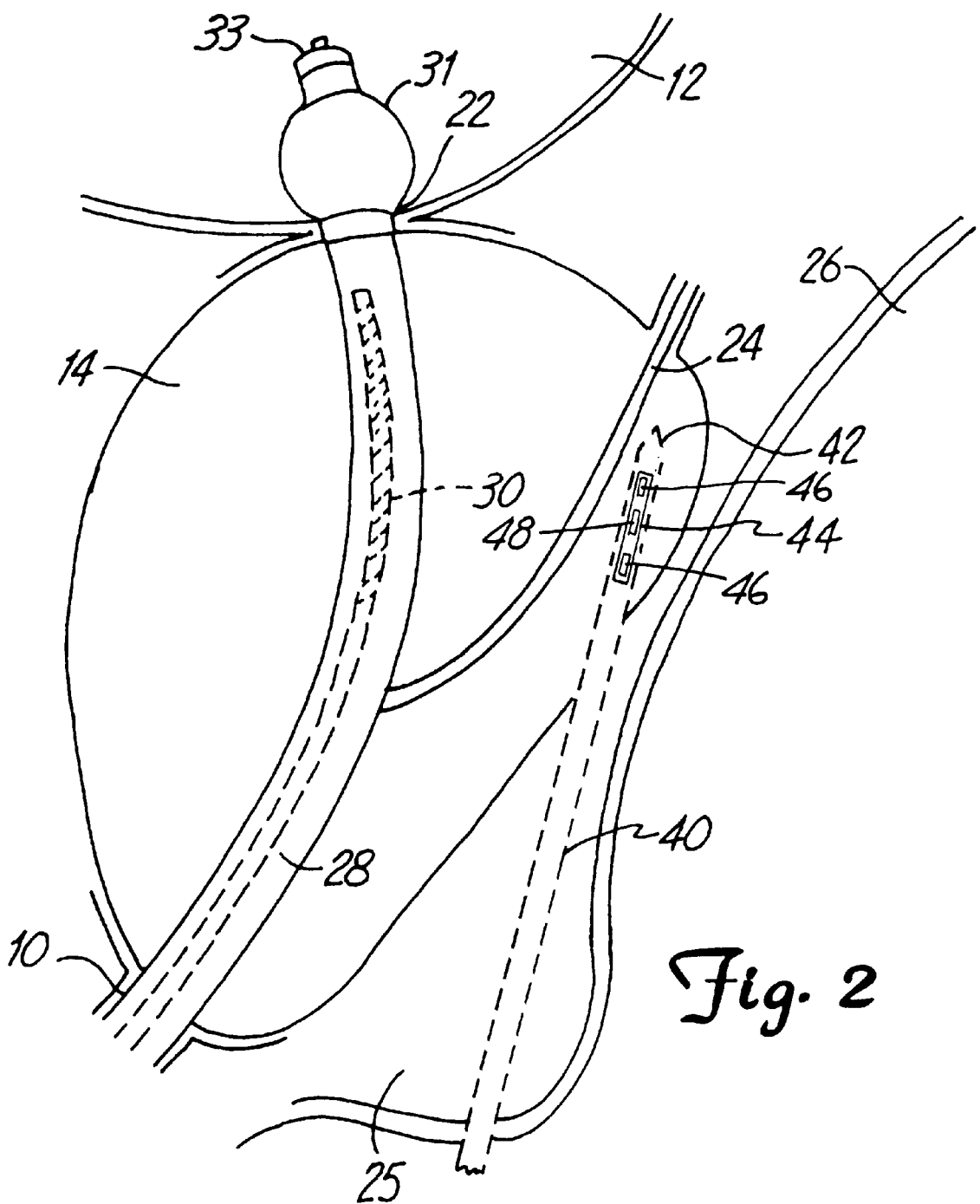
FIG. 2 is an enlarged view of the male pelvic region of FIG. 1, illustrating the treatment apparatus and method of the present invention.

FIG. 2 shows an enlarged view of the male pelvic region of FIG. 1, illustrating the treatment apparatus and method of the present invention. Probe 28 containing microwave antenna 30 is properly positioned within urethra 10 in a manner known in the art. As is known in the art, retention balloon 31 at distal end 33 of probe 28 is inflatable in bladder 12 to secure probe 28 at a predetermined axial location of urethra 10. A detailed discussion of the preferred structure and operation of microwave antenna 30 within probe 28 may be found in the aforementioned U.S. Pat. No. 5,330,518.

Transperineal needle 40 is shown schematically in FIG. 2 for simplicity, and includes tip 42 and cartridge 44. In an exemplary embodiment, cartridge 44 contains seeds 46 and X-ray opaque marker 48, and is constructed in a manner known in the art. Needle 40 is hollow and is insertable into perineum 25 to position cartridge 44 proximate the outer capsule of prostate 14, at which point cartridge 44 is permanently implanted in prostate 14 and needle 40 is removed, as is known in the art. Needle 40 is accordingly shown in dashed lines in FIG. 2 to signify that it is not located in prostate 14 during treatment. In an exemplary embodiment, cartridge 44 is composed of purified titanium or another material known in the art for isolating seeds 46 from interacting with body tissue. Seeds 46 may for example be composed of a radioactive material such as Palladium-103 or Iodine-125, or of a non-radioactive material that elevates in temperature when placed in a magnetic field such as Cobalt Palladium, the properties of these materials to treat cancer being known in the art. Alternatively, other radioactive and thermal materials may be used to realize seeds 46 for treating cancerous tissue in the vicinity of needle 40. X-ray opaque marker 48 is provided to enable visualization of the location of cartridge 44 within the body during and after implantation, with externally generated X-rays being used to provide visual images of internal portions of the body in a manner known in the art.

In operation, probe 28 and cartridge 44 are each positioned in urethra 10 and prostate 14, respectively. Although probe 28 may potentially be inserted at the same time that needle 40 is inserted into perineum 25 to implant cartridge 44, it is typically more practical to insert probe 28 and needle 40 separately. Once probe 28 is inserted in urethra 10, microwave antenna 30 is energized in a manner sufficient to heat a volume of prostate tissue to a temperature of greater than about 45° C. for a time sufficient to necrose the prostate tissue while preserving the tissue of the urethral wall. Less than about an hour of energization of microwave antenna 30 is typically required to necrose the volume of prostate tissue, but the therapy may be extended or shortened depending on the therapeutic dose required to treat the particular patient's condition. However, due to several factors such as the vascularity of the prostate and its effect on conductive heating, the burden on the cooling system associated with probe 28 to preserve the urethral wall when microwave power is increased, and the inability to precisely control the boundaries of therapeutic temperatures (to preserve rectum 26, for example), the volume of tissue that is heated to therapeutic temperatures (above about 45° C.) may not extend completely to the periphery of the prostate, which could leave cancerous tissue located in that portion of the prostate untreated. In order to ensure that cancerous tissue in all regions of the prostate is treated, the thermal therapy is supplemented by energy delivered from seeds 46 in cartridge 44. When cartridge 44 is implanted in prostate 14, seeds 46 emit ionizing radiation or thermal energy to necrose prostate tissue in the immediate vicinity of cartridge 44, at the outer capsule of prostate 14. Where radioactive seeds are used, seeds 46 gradually decompose as they emit radiation, which is a process the duration of which depends on the radioactive isotope utilized in cartridge 44. For example, Palladium-103 has a half-life of about 17 days, and Iodine-125 has a half-life of about 60 days. Where thermal seeds are used, seeds 46 only elevate in temperature in the presence of a magnetic field, which may be supplied from an external source for a time period sufficient to heat the portion of prostate 14 in the inunediate vicinity of seeds 46 to temperatures above about 45° C. to necrose the tissue, for example.

In one embodiment, a temperature sensor may be carried by a probe such as 40 to provide detailed information on the temperature of prostate tissue adjacent rectum 26. This information may be used to control the power delivered from the microwave antenna 30 so that the periphery of prostate 14 may be heated to therapeutic temperatures while controlling temperatures at rectum 26 to prevent thermal damage. The temperature sensor may be provided in addition to, or as a replacement for, the radiation-emitting seeds implanted by probe 40. The probe (such as 40) carrying the temperature sensor is maintained in the target volume of prostate tissue throughout the therapy session, with a mechanism provided to communicate the data from the temperature sensor to a control system that controls the therapy. After the therapy session is complete, the probe containing the temperature sensor may be removed.

The two treatment modalities disclosed herein complement one another, supplementing the thermal therapy effected by probe 28 to ensure full necrosis of targeted cancerous prostate tissue all the way to the outer capsule of prostate 14, while still preserving the wall of urethra 10 with a conventional cooling system. The majority of prostate 14 is treated by thermal therapy delivered from probe 28. Only a relatively small portion of prostate 14 (including at least the portion of prostate 14 that is not necrosed by thermal therapy from probe 28) is treated by energy delivered from seeds 46 implanted in prostate 14. Seed therapy alone requires a multitude of needles and implanted seeds to treat the entire prostate, which is highly invasive and increases the risk of post-treatment effects such as acute urinary retention and dysuria, and due to the effects of radiation may result in morbidity symptoms such as impotence and incontinence. In addition, the radioactive seeds and application procedure are quite expensive, often more expensive than surgery. Utilizing thermal therapy supplemented with interstitial seed therapy according to the present invention greatly reduces the number of punctures in perineum 25 that are required, since the volume of prostate tissue that must be treated by the seed therapy is substantially less, and requires lower levels of radiation. As a result, the thermal therapy procedure supplemented by seed therapy is only minimally invasive, and the risk of negative effects and symptoms is significantly lessened. Also, less seeds are required and the application procedure is simplified, reducing the total cost associated with the therapy.

The present invention has been described as it applies to prostate cancer; however, it will be apparent to one skilled in the art that certain principles and teachings disclosed herein are also applicable to treatment of other cancers.

Although the present invention has been described with reference to preferred embodiments, workers skilled in the art will recognize that changes may be made in form and detail without departing from the spirit and scope of the invention.

What is claimed is:

1. A method of treating a target volume of cancerous tissue comprising:

positioning a probe carrying a microwave antenna in a body cavity proximate the target volume;

placing at least one energy-emitting element in the target volume; and energizing the microwave antenna, whereby energy emitted from the antenna and the energy-emitting element necroses cancerous tissue in the target volume.

2. The method of claim 1, wherein the at least one energy-emitting element comprises at least one radiation-emitting seed.

3. The method of claim 1, wherein the at least one energy-emitting element comprises at least one seed that elevates in temperature in the presence of a magnetic field.

4. The method of claim 1, wherein the step of placing the energy-emitting element comprises inserting a needle through a perineum to implant the energy-emitting element in the target volume.

5. The method of claim 1, wherein the step of positioning the probe comprises inserting the probe into a urethra, and the target volume is a volume of prostate tissue that includes tissue proximate an outer capsule of a prostate.

6. A system for treating a target volume of cancerous tissue comprising:
   a probe adapted to be inserted into a body cavity proximate the target volume;
   a microwave antenna carried by the probe;
   a needle adapted to be inserted through a perineum into the target volume; and
   an energy-emitting element carried by the needle for implantation in the target volume.

7. The system of claim 6, wherein the energy-emitting element comprises a radiation-emitting seed.

8. The system of claim 6, wherein the energy-emitting element comprises a seed that elevates in temperature in the presence of a magnetic field.

9. The system of claim 6, wherein the probe is adapted to be inserted into a urethra, and the target volume comprises a volume of prostate tissue that includes tissue proximate an outer capsule of a prostate.

10. A method of treating a target volume of cancerous tissue comprising:
    positioning a treatment probe carrying a microwave antenna in a body cavity proximate the target volume;
    inserting a temperature sensing probe separate from the treatment probe into the target volume, the temperature sensing a probe including at least one temperature sensor positioned in the target volume;
    energizing the microwave antenna to thermally treat the cancerous tissue in the target volume;
    controlling power delivered to the microwave antenna based on data from the temperature sensor positioned in the targtet volume; and
    placing at least one energy-emitting element in the target volume, whereby energy emitted from the antenna and the energy-emitting element necroses the cancerous tissue in the target volume.

11. A method of treating cancerous tissue in a prostate, the method comprising:
    positioning a catheter carrying a microwave antenna in a urethra proximate the prostate;
    positioning at least one temperature sensor in the prostate distant from the urethra and adjacent a rectum;
    energizing the microwave antenna to thermally treat the cancerous tissue in the prostate;
    controlling power delivered to the microwave antenna based on data from the temperature sensor positioned in the prostate, so that a periphery of the prostate is heated to therapeutic temperatures while controlling temperatures at the rectum to prevent thermal damage to the rectum; and
    placing at least one energy-emitting element in the prostate, whereby energy emitted from the antenna and the energy-emitting element necroses the cancerous tissue in the prostate.

* * * * *